US006951830B2

(12) United States Patent
Janssen

(10) Patent No.: US 6,951,830 B2
(45) Date of Patent: Oct. 4, 2005

(54) MOLECULAR SIEVE CATALYST COMPOSITIONS, THEIR PRODUCTION AND USE IN CONVERSION PROCESSES

(75) Inventor: Marcel J. G. Janssen, Kessel Lo (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/634,557

(22) Filed: Aug. 6, 2003

(65) Prior Publication Data

US 2005/0032632 A1 Feb. 10, 2005

(51) Int. Cl.⁷ .............................. B01J 29/83; B01J 29/85
(52) U.S. Cl. ......................... 502/84; 502/208; 502/214; 502/80
(58) Field of Search ............................... 502/68, 73, 80, 502/84, 208, 214

(56) References Cited

U.S. PATENT DOCUMENTS

| 4,062,905 A | 12/1977 | Chang et al. ............... 260/682 |
| 4,079,095 A | 3/1978 | Givens et al. .............. 260/682 |
| 4,310,440 A | 1/1982 | Wilson et al. .............. 252/435 |
| 4,440,871 A | 4/1984 | Lok et al. .................... 502/214 |
| 4,499,327 A | 2/1985 | Kaiser ......................... 585/640 |
| 4,677,242 A | 6/1987 | Kaiser ......................... 585/638 |
| 4,677,243 A | 6/1987 | Kaiser ......................... 585/638 |
| 4,873,390 A | 10/1989 | Lewis et al. ................ 585/638 |
| 4,889,615 A | 12/1989 | Chin et al. ................... 208/113 |
| 5,095,163 A | 3/1992 | Barger ......................... 585/640 |
| 5,367,100 A | 11/1994 | Gongwei et al. ........... 585/640 |
| 5,714,662 A | 2/1998 | Vora et al. ................... 585/640 |
| 6,010,619 A | 1/2000 | Wise et al. .................. 208/120 |
| 6,162,350 A | * 12/2000 | Soled et al. ................. 208/113 |
| 6,166,282 A | 12/2000 | Miller ......................... 585/638 |
| 6,180,828 B1 | 1/2001 | Hidaka et al. .............. 564/479 |
| 2004/0097770 A1 | * 5/2004 | Dakka et al. ............... 585/467 |

FOREIGN PATENT DOCUMENTS

| EP | 0 278 535 | 8/1988 | |
| EP | 0 312 981 | 4/1989 | ........... C01G/11/05 |
| EP | 1 314 474 A | 5/2003 | .......... B01J/27/232 |
| WO | WO 98/29370 | 9/1998 | ........... C07C/11/02 |
| WO | WO 03/000412 A1 | 1/2003 | |
| WO | WO 03/074175 | 9/2003 | ............ B01J/29/00 |
| WO | WO 01/38271 | * 5/2004 | |

OTHER PUBLICATIONS

U.S. Appl. No. 10/364,156, filed Feb. 10, 2003, Levin et al.
Kang and Inui, Effects of Decrease in Number of Acid Sites Located on the External Surface of N1–SAPO–34 Crystalline Catalyst by Mechanochemical Method, Catalyst Letters 53, pp. 171–176 (1998).

* cited by examiner

Primary Examiner—Christina Johnson

(57) ABSTRACT

The invention relates to a catalyst composition, a method of making the same and its use in the conversion of a feedstock, preferably an oxygenated feedstock, into one or more olefin (s), preferably ethylene and/or propylene The catalyst composition a molecular sieve, such as a silicoaluminophosphate and/or an aluminophosphate, hydrotalcite, and optionally a rare earth metal component

33 Claims, No Drawings

MOLECULAR SIEVE CATALYST COMPOSITIONS, THEIR PRODUCTION AND USE IN CONVERSION PROCESSES

FIELD

The present invention relates to molecular sieve catalyst compositions, to the production of such compositions and to the use of such compositions in conversion processes, particularly to produce olefin(s).

BACKGROUND

Olefins are traditionally produced from petroleum feedstocks by catalytic or steam cracking processes. These cracking processes, especially steam cracking, produce light olefin(s), such as ethylene and/or propylene, from a variety of hydrocarbon feedstocks. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids or carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Other known syngas production processes include conventional steam reforming, autothermal reforming, or a combination thereof.

Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred process for converting a feedstock containing methanol into one or more olefin(s), primarily ethylene and/or propylene, involves contacting the feedstock with a molecular sieve catalyst composition.

There are many different types of molecular sieve well known to convert a feedstock, especially an oxygenate containing feedstock, into one or more olefin(s). For example, U.S. Pat. No. 5,367,100 describes the use of the zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; and U.S. Pat. No. 4,310,440 describes producing light olefin(s) from an alcohol using a crystalline aluminophosphate, often designated AlPO4.

Some of the most useful molecular sieves for converting methanol to olefin(s) are silicoaluminophosphate molecular sieves. Silicoaluminophosphate (SAPO) molecular sieves contain a three-dimensional microporous crystalline framework structure of [SiO4], [AlO4] corner sharing tetrahedral units. SAPO synthesis is described in U.S. Pat. No. 4,440,871, which is herein fully incorporated by reference. SAPO molecular sieves are generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, are disclosed in U.S. Pat. Nos. 4,499,327, 4,677,242, 4,677,243, 4,873,390, 5,095,163, 5,714,662 and 6,166,282, all of which are herein fully incorporated by reference.

Typically, molecular sieves are formed into molecular sieve catalyst compositions to improve their durability in commercial conversion processes. These molecular sieve catalyst compositions are formed by combining the molecular sieve with a matrix material and/or a binder, which typically are metal oxides. However, these binders and matrix materials typically only serve to provide desired physical characteristics to the catalyst composition, and have little to no effect on conversion and selectivity of the molecular sieve. It would therefore be desirable to have an improved molecular sieve catalyst composition having a better conversion rate, improved olefin selectivity and a longer lifetime.

U.S. Pat. No. 4,889,615 discloses a process for the catalytic cracking of high metals content feeds, including resids, in which the feed is cracked in the presence of a catalyst comprising a zeolite, such as zeolite Y, and an additive comprising a dehydrated magnesium-aluminum hydrotalcite which acts as a trap for vanadium as well as an agent for reducing the content of sulfur oxides in the regenerator flue gas.

U.S. Pat. No. 6,010,619 discloses a fluid catalytic cracking process for converting hydrocarbon feed stocks containing heavy metal compounds, in which the catalyst employed comprises a zeolite or silicophosphoaluminate treated with particles of a carbonated strontium-substituted hydrotalcite.

U.S. Pat. No. 6,180,828 discusses the use of a modified molecular sieve to produce methylamines from methanol and ammonia where, for example, a silicoaluminophosphate molecular sieve is combined with one or more modifiers, such as a zirconium oxide, a titanium oxide, an yttrium oxide, montmorillonite or kaolinite.

EP-A-3 12981 discloses a process for cracking vanadium-containing hydrocarbon feed streams using a catalyst composition comprising a physical mixture of a zeolite embedded in an inorganic refractory matrix material and at least one oxide of beryllium, magnesium, calcium, strontium, barium or lanthanum, preferably magnesium oxide, on a silica-containing support material.

Kang and Inui, Effects of decrease in number of acid sites located on the external surface of Ni-SAPO-34 crystalline catalyst by the mechanochemical method, Catalysis Letters 53, pages 171–176 (1998) disclose that the shape selectivity can be enhanced and the coke formation mitigated in the conversion of methanol to ethylene over Ni-SAPO-34 by milling the catalyst with MgO, CaO, BaO or Cs2O on microspherical non-porous silica, with BaO being the most preferred.

International Publication No. WO 98/29370 discloses the conversion of oxygenates to olefins over a small pore non-zeolitic molecular sieve containing a metal selected from the group consisting of a lanthanide, an actinide, scandium, yttrium, a Group 4 metal, a Group 5 metal or combinations thereof.

In our co-pending U.S. patent application Ser. No. 10/364,156 filed Feb. 10, 2003, there is described catalyst composition which exhibits enhanced lifetime when used in the conversion of oxygenates to olefins and which comprises a molecular sieve and at least one metal oxide having an uptake of carbon dioxide at 100° C. of at least 0.03 mg/m2 of the metal oxide. The metal oxide is selected from an oxide of Group 4 of the Periodic Table of Elements, either alone or in combination with an oxide selected from Group 2 of the Periodic Table of Elements and/or an oxide selected from Group 3 of the Periodic Table of Elements, including the Lanthanide series of elements and the Actinide series of elements.

SUMMARY

In one embodiment, the invention provides a catalyst composition including a molecular sieve, hydrotalcite, and a rare earth metal component. In one aspect of this embodiment, the molecular sieve is selected from an aluminophosphate, a silicoaluminophosphate and metal-containing forms thereof. In a particular aspect of this embodiment, the rare earth metal is lanthanum.

Conveniently, the molecular sieve is selected from SAPO-5, SAPO-8, SAPO-11, SAPO-16, SAPO-17, SAPO-18, SAPO-20, SAPO-3 1, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, MCM-2, metal-containing forms thereof and mixtures, including intergrowths, thereof. Particularly useful molecular sieves include SAPO-18, SAPO-34, SAPO-35, SAPO-44, SAPO-47, AlPO-34, metal-containing forms thereof, and mixtures, including intergrowths, thereof, especially SAPO-34, intergrowths of SAPO-34 and SAPO-1 8, and intergrowths of GeAPO-34 and GeAPO-18.

In another embodiment, the invention provides a catalyst composition including an aluminophosphate or silicoaluminophosphate molecular sieve selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, MCM-2, metal-containing forms thereof, and mixtures, including intergrowths, thereof and hydrotalcite. Optionally, the composition can further include a rare earth metal component, such as lanthanum.

Conveniently, the aluminophosphate and metallcoaluminophosphate molecular sieves are selected from AlPO-5, AlPO-11, AlPO-18, AlPO-31, AlPO-34, AlPO-36, AlPO-37, AlPO-46, metal-containing forms thereof and mixtures, including intergrowths, thereof.

In yet another embodiment, the invention provides a process for formulating a molecular sieve catalyst composition, the process including providing a molecular sieve; providing a hydrotalcite composition including hydrotalcite and rare earth metal component; and combining the molecular sieve and the hydrotalcite composition to produce a formulated molecular sieve catalyst composition.

Conveniently, the step of providing a hydrotalcite composition is carried out by providing a solution of a rare earth metal compound; mixing the solution with hydrotalcite to form a slurry; and drying the slurry to form a dried hydrotalcite composition. By way of example, the rare earth metal compound may be a halide, an oxide, an oxyhalide, a hydroxide, a sulfide, a sulfonate, a boride, a borate, a carbonate, a nitrate, a carboxylate or a mixture thereof.

Conveniently, the step of combining the molecular sieve and the hydrotalcite composition is carried out by forming a slurry of the molecular sieve and the hydrotalcite composition; and drying the slurry to form a dried, formulated molecular sieve catalyst composition.

In further embodiment, the invention provides a process for converting a hydrocarbon oxygenate feedstock to olefins, the process comprising contacting the feedstock with a catalyst composition comprising:

(a) molecular sieve; and (b) hydrotalcite;

under catalytic conversion conditions, to form a product mixture comprising olefins.

DETAILED DESCRIPTION OF THE EMBODIMENTS

Introduction

The invention is directed to a molecular sieve catalyst composition, its production and its use in the conversion of hydrocarbon feedstocks, particularly oxygenated feedstocks, into olefin(s). It has been found that combining a molecular sieve with hydrotalcite, optionally together with a rare earth metal, results in a catalyst composition with a longer lifetime when used in the conversion of feedstocks, such as oxygenates, more particularly methanol, into olefin (s). In addition, the resultant catalyst composition tends to be more propylene selective than the same molecular sieve without the hydrotalcite additive.

Molecular Sieves

Molecular sieves have been classified by the Structure Commission of the International Zeolite Association according to the rules of the IUPAC Commission on Zeolite Nomenclature. According to this classification, crystalline molecular sieves, for which a structure has been established, are assigned a three letter code and are described in the Atlas of Zeolite Framework Types, 5th edition, Elsevier, London, England (2001), which is herein fully incorporated by reference.

Crystalline molecular sieves all have a 3-dimensional, four-connected framework structure of corner-sharing [TO4] tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pages 1–67, Elsevier Science, B.V., Amsterdam, Netherlands (2001).

Non-limiting examples of molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of preferred molecular sieves, particularly for converting an oxygenate containing feedstock into olefin (s), include AEL, AFY, AEI, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

The small, medium and large pore molecular sieves have from a 4-ring to a 12-ring or greater framework-type. In one embodiment, the molecular sieves used herein have 8-, 10- or 12-ring structures and an average pore size in the range of from about 3 Å to 15 Å. In a more preferred embodiment, the molecular sieves have 8-rings and an average pore size less than about 5 Å, such as in the range of from 3 Å to about 5 Å, for example from 3 Å to about 4.5 Å, and particularly from 3.5 Å to about 4.2 Å.

Molecular sieves have a molecular framework including one, or preferably, two or more corner-sharing [TO4] tetrahedral units, and more preferably, two or more [SiO4], [AlO4] and/or [PO4] tetrahedral units. Typically, the molecular sieves used herein are aluminophosphate (AlPO) molecular sieves, silicoaluminophosphate (SAPO) molecular sieves, metal-containing AlPO and SAPO molecular sieves and intergowths of such sieves.

In the case of metal-containing molecular sieves, the metal atoms can be inserted into the framework of the molecular sieve through a tetrahedral unit, such as [MeO2], and carry a net charge depending on the valence state of the metal substituent. For example, in one embodiment, when the metal substituent has a valence state of +2, +3, +4, +5, or +6, the net charge of the tetrahedral unit is between –2 and +2.

Examples of suitable metals for use in the metal-containing molecular sieves used herein are alkali metals of Group 1 of the Periodic Table of Elements, alkaline earth metals of Group 2 of the Periodic Table of Elements, rare earth metal of Group 3 of the Periodic Table of Elements, including the Lanthanides: lanthanum, cerium, praseodymium, neodymium, samarium, europium, gadolinium, terbium, dysprosium, holmium, erbium, thulium, ytterbium and lutetium; and scandium or yttrium, transition metals of Groups 4 to 12 of the Periodic Table of Elements, and mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. The Periodic Table of Elements referred to herein is the IUPAC format described in the CRC Handbook of Chemistry and Physics, 78th Edition, CRC Press, Boca Raton, Fla. (1997).

Aluminophosphate molecular sieves, silicoaluminophosphate molecular sieves and metal containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO), EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in R. Szostak, Handbook of Molecular Sieves, Van Nostrand Reinhold, New York, N.Y. (1992), which is herein fully incorporated by reference.

In one embodiment, the molecular sieve, as described in many of the U.S. Patents mentioned above, is represented by the empirical formula, on an anhydrous basis:

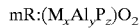

$$mR:(M_xAl_yP_z)O_2$$

wherein R represents at least one templating agent, preferably an organic templating agent; m is the number of moles of R per mole of $(M_xAl_yP_z)O_2$ and has a value from 0 to 1, preferably 0 to 0.5, and most preferably from 0 to 0.3; x, y, and z represent the mole fraction of Al, P and M as tetrahedral oxides, where M is an element selected from one of Groups 1, 2, 3, 4, 5, 6, 7, 8, 9, 10, 11, 12, 13, 14 and Lanthanide's of the Periodic Table of Elements. Preferably M is selected from Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-3 1, SAPO-34, SAPO-35, SAPO-36, SAPO-37, SAPO-40, SAPO-41, SAPO-42, SAPO-44 (U.S. Pat. No. 6,162,415), SAPO-47, SAPO-56, AlPO-5, AlPO-11, AlPO-18, AlPO-31, AlPO-34, AlPO-36, AlPO-37, AlPO-46, MCM-2 and metal containing molecular sieves thereof. Of these, particularly useful molecular sieves are one or a combination of SAPO-18, SAPO-34, SAPO-35, SAPO-44, SAPO-56, AlPO-18 and AlPO-34 and metal containing derivatives thereof, such as one or a combination of SAPO-18, SAPO-34, AlPO-34 and AlPO-18, and metal containing derivatives thereof, such as GeAPO-34 and GeAPO-18.

In an embodiment, the molecular sieve is an intergrowth material having two or more distinct crystalline phases within one molecular sieve composition. In particular, intergrowth molecular sieves are described in the U.S. Patent Application Publication No. 2002/0165089 and International Patent Publication No. WO 98/15496, both of which are herein fully incorporated by reference. For example, SAPO-18, AlPO-18 and RUW-18 have an AEI framework-type, and SAPO-34 has a CHA framework-type. Thus the molecular sieve used herein may comprise at least one intergrowth phase of AEI and CHA framework-types, especially where the ratio of CHA framework-type to AEI framework-type, as determined by the DIFFaX method disclosed in U.S. Patent Application Publication No. 2002/0165089, is greater than 1:1.

Molecular Sieve Synthesis

The synthesis of molecular sieves is described in many of the references discussed above. Generally, molecular sieves are synthesized by the hydrothermal crystallization of one or more of a source of aluminum, a source of phosphorus, a source of silicon and a templating agent, such as a nitrogen containing organic compound. Typically, a combination of sources of silicon, aluminum and phosphorus, optionally with one or more templating agents, is placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

Non-limiting examples of silicon sources include silicates, fumed silica, for example, Aerosil-200 available from Degussa Inc., New York, N.Y., and CAB-O-SIL M-5, organosilicon compounds such as tetraalkyl orthosilicates, for example, tetramethyl orthosilicate (TMOS) and tetraethylorthosilicate (TEOS), colloidal silicas or aqueous suspensions thereof, for example Ludox HS-40 sol available from E.I. du Pont de Nemours, Wilmington, Del., silicic acid or any combination thereof.

Non-limiting examples of aluminum sources include aluminum alkoxides, for example aluminum isopropoxide, aluminum phosphate, aluminum hydroxide, sodium aluminate, pseudo-boehmite, gibbsite and aluminum trichloride, or any combination thereof. A convenient source of aluminum is pseudo-boehmite, particularly when producing a silicoaluminophosphate molecular sieve.

Non-limiting examples of phosphorus sources, which may also include aluminum-containing phosphorus compositions, include phosphoric acid, organic phosphates such as triethyl phosphate, and crystalline or amorphous aluminophosphates such as AlPO4, phosphorus salts, or combinations thereof. A convenient source of phosphorus is phosphoric acid, particularly when producing a silicoaluminophosphate.

Templating agents are generally compounds that contain elements of Group 15 of the Periodic Table of Elements, particularly nitrogen, phosphorus, arsenic and antimony. Typical templating agents also contain at least one alkyl or aryl group, such as an alkyl or aryl group having from 1 to 10 carbon atoms, for example from 1 to 8 carbon atoms. Preferred templating agents are often nitrogen-containing compounds, such as amines, quaternary ammonium compounds and combinations thereof. Suitable quaternary ammonium compounds are represented by the general formula R4N+, where each R is hydrogen or a hydrocarbyl or substituted hydrocarbyl group, preferably an alkyl group or an aryl group having from 1 to 10 carbon atoms.

Non-limiting examples of templating agents include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methylpyridine, quinuclidine, N,N'-dimethyl-1,4-diazabicyclo(2,2,2)octane ion; di-n-butylamine, neopentylamine, di-n-pentylamine, isopropylamine, t-butylamine, ethylenediamine, pyrrolidine, and 2-imidazolidone.

The pH of the synthesis mixture containing at a minimum a silicon-, aluminum-, and/or phosphorus-composition, and a templating agent, is generally in the range of from 2 to 10, such as from 4 to 9, for example from 5 to 8.

Generally, the synthesis mixture described above is sealed in a vessel and heated, preferably under autogenous pressure, to a temperature in the range of from about 80° C. to about 250° C., such as from about 100° C. to about 250° C., for example from about 125° C. to about 225° C., such as from about 150° C. to about 180° C.

In one embodiment, the synthesis of a molecular sieve is aided by seeds from another or the same framework type molecular sieve.

The time required to form the crystalline product is usually dependent on the temperature and can vary from immediately up to several weeks. Typically the crystallization time is from about 30 minutes to around 2 weeks, such as from about 45 minutes to about 240 hours, for example from about 1 hour to about 120 hours. The hydrothermal crystallization may be carried out with or without agitation or stirring.

Once the crystalline molecular sieve product is formed, usually in a slurry state, it may be recovered by any standard technique well known in the art, for example, by centrifugation or filtration. The recovered crystalline product may then be washed, such as with water, and then dried, such as in air.

One method for crystallization involves producing an aqueous reaction mixture containing an excess amount of a templating agent, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Other methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001 (freeze drying the molecular sieve), which are all herein fully incorporated by reference.

Where a templating agent is used in the synthesis of the molecular sieve, any templating agent retained in the product may be removed after crystallization by numerous well known techniques, for example, by calcination. Calcination involves contacting the molecular sieve containing the templating agent with a gas, preferably containing oxygen, at any desired concentration at an elevated temperature sufficient to either partially or completely remove the templating agent.

Aluminosilicate and silicoaluminophosphate molecular sieves have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, such as less than 0.40, for example less than 0.32, and particularly less than 0.20. In another embodiment the molecular sieve has a Si/Al ratio in the range of from about 0.65 to about 0.10, such as from about 0.40 to about 0.10, for example from about 0.32 to about 0.10, and particularly from about 0.32 to about 0.15.

Hydrotalcite Additive

Naturally occurring hydrotalcite is a mineral found in relatively small quantities in a limited number of geographical areas, principally, in Norway and in the Ural Mountains. Natural hydrotalcite has a variable composition depending on the location of the source. Natural hydrotalcite is a hydrated magnesium, aluminum and carbonate-containing composition, which has been found to have the typical composition, represented as Mg6Al2(OH)16CO3.4H2O. Natural hydrotalcite deposits are generally found intermeshed with spinel and other minerals, such as penninite and muscovite, from which it is difficult to separate the natural hydrotalcite.

Synthetically produced hydrotalcite can be made to have the same composition as natural hydrotalcite, or, because of flexibility in the synthesis, it can be made to have a different composition by replacing the carbonate anion with other anions, such as phosphate ion. In addition, the Mg/Al ratio can be varied to control the basic properties of the hydrotalcite.

A phosphate-modified synthetic hydrotalcite and a process for its synthesis are disclosed in U.S. Pat. No. 4,883,533. U.S. Pat. No. 3,539,306 discloses a process for preparing hydrotalcite which involves mixing an aluminum-containing compound with a magnesium-containing compound in an aqueous medium in the presence of carbonate ion at a pH of at least 8. U.S. Pat. No. 4,656,156 discloses a process for producing synthetic hydrotalcite by heating a magnesium compound to a temperature of about 500 to 900° C. to form activated magnesia, adding the activated magnesia to an aqueous solution containing aluminate, carbonate and hydroxyl ions, and then agitating the resultant mixture at a temperature of about 80 to 100° C. for 20 to 120 minutes to form a low density, high porosity hydrotalcite. A similar process is disclosed in U.S. Pat. No. 4,904,457. The entire disclosure of each of the above references is incorporated herein by reference.

Hydrotalcite compositions containing pillaring organic, inorganic and mixed organic/inorganic anions are disclosed in U.S. Pat. No. 4,774,212, the entire disclosure of which is incorporated herein by reference. The compositions are anionic magnesium aluminum hydrotalcite clays having large inorganic and/or organic anions located interstitially between positively charged layers of metal hydroxides. The compositions are of the formula:

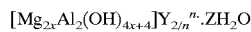

where Y is a large organic anion selected from the group consisting of lauryl sulfate, p-toluenesulfonate, terephthalate, 2,5-dihydroxy-1,4-benzenedisulfonate, and 1,5-naphthalenedisulfonate or where Y is an anionic polyoxometalate of vanadium, tungsten or molybdenum. In the above cases, x is from 1.5 to 2.5, n is 1 or 2 and Z is from 0 to 3, except that when Y is polyoxometalate, n is 6.

An aggregated synthetic hydrotalcite having a substantially spheroidal shape and an average spherical diameter of up to about 60 $\mu$m, composed of individual platy particles, is disclosed in U.S. Pat. No. 5,364,828, the entire disclosure of which is incorporated herein by reference. This form of hydrotalcite is prepared from aqueous solutions of soluble magnesium and aluminum salts, which are mixed in a molar ratio of from about 2.5:1 to 4:1, together with a basic solution containing at least a two-fold excess of carbonate and a sufficient amount of a base to maintain a pH of the reaction mixture in the range of from about 8.5 to about 9.5.

Synthetic hydrotalcite is commercially available and can, for example, be obtained from Sasol North America Inc. as Condea Pural MG70.

Prior to use in the catalyst composition of the invention, it may be desirable to calcine the hydrotalcite to remove the water inherently contained by the material. Suitable calcination conditions include a temperature of from about 300° C. to about 800° C., such as from about 400° C. to about 600° C. for about 1 to about 16 hours, such as for about 3 to about 8 hours.

Rare Earth Metal Component

In addition to the hydrotalcite additive, the molecular sieve catalyst composition of the invention can also include a rare earth metal component. Suitable rare earth metals include yttrium and elements of the Lanthanide or Actinide series metals, including lanthanum, cerium, praseodymium, neodymium, samarium, europium, gadolinium, terbium, dysprosium, holmium, erbium, thulium, ytterbium, lutetium, thorium and mixtures thereof. Typically the rare earth metal will be selected from lanthanum, yttrium, cerium and mixtures thereof, especially lanthanum.

The rare earth metal component can be present in the final catalyst composition as the elemental rare earth metal or more preferably, as an oxide of the metal.

Catalyst Composition

The catalyst composition of the invention includes any one of the molecular sieves previously described, hydrotalcite and optionally a rare earth metal component. Typically, the catalyst composition contains in the range of from about 10 wt % to about 90 wt %, such as from about 40 wt % to about 60 wt %, of the molecular sieve and in the range of from about 10 wt % to about 90 wt %, such as from about 40 wt % to about 60 wt %, of the hydrotalcite based on the total weight of the molecular sieve, the hydrotalcite, and any rare earth metal component present.

Moreover, where the catalyst composition contains a rare earth metal component, said rare earth metal component is typically present in the range of from about 0.1 wt % to about 5 wt %, such as from about 1 wt % to about 3 wt %, based on the total weight of the molecular sieve, the hydrotalcite, and rare earth metal component.

In addition, the catalysts composition can contain a binder and/or matrix material to enhance the physical characteristics of the catalyst.

There are many different binders that are useful in forming catalyst compositions. Non-limiting examples of binders that are useful alone or in combination include various types of hydrated alumina, silicas, and/or other inorganic oxide sols. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide binder component. For example, an alumina sol will convert to an aluminum oxide binder following heat treatment.

Aluminum chlorhydrol, a hydroxylated aluminum based sol containing a chloride counter ion, has the general formula of AlmOn(OH)oClp.x(H2O) wherein m is 1 to 20, n is 1 to 8, o is 5 to 40, p is 2 to 15, and x is 0 to 30. In one embodiment, the binder is Al13O4(OH)24Cl7.12(H2O) as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binder is an alumina sol, predominantly comprising aluminum oxide, optionally including some silicon. In yet another embodiment, the binder is peptized alumina made by treating an alumina hydrate, such as pseudobohemite, with an acid, preferably an acid that does not contain a halogen, to prepare a sol or aluminum ion solution. Non-limiting examples of commercially available colloidal alumina sols include Nalco 8676 available from Nalco Chemical Co., Naperville, Ill., and Nyacol AL20DW available from Nyacol Nano Technologies, Inc., Ashland, Mass.

Non-limiting examples of matrix materials include one or more non-active metal oxides including beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include haloysite, kaolinite, dickite, nacrite, or anauxite. The matrix material, such as a clay, may be subjected to well known modification processes such as calcination and/or acid treatment and/or chemical treatment.

Where the catalyst composition contains a binder and/or matrix material, the catalyst composition typically contains from about 1% to about 80%, such as from about 5% to about 60%, and particularly from about 5% to about 50%, by weight of the molecular sieve based on the total weight of the catalyst composition. Where the catalyst composition contains a binder and a matrix material, the weight ratio of the binder to the matrix material is typically from 1:15 to 1:5, such as from 1:10 to 1:4, and particularly from 1:6 to 1:5.

Method of Making the Catalyst Composition

The catalyst composition used herein can be prepared using a variety of methods. In general, however, making the catalyst composition comprises initially synthesizing the molecular sieve and then combining the molecular sieve with a hydrotalcite composition comprising the hydrotalcite and, where desired, a rare earth metal component. Combining the molecular sieve with a hydrotalcite composition is conveniently achieved by forming a slurry of the molecular sieve and the hydrotalcite composition in a liquid, mixing the slurry, for example by colloid milling, to produce a substantially homogeneous mixture and then drying the mixture. Non-limiting examples of suitable liquids include one or a combination of water, alcohol, ketones, aldehydes, and/or esters. The most preferred liquid is water.

Where the hydrotalcite composition contains a rare earth metal component, it is conveniently produced by dissolving a rare earth compound in a solvent, such as water, combining the resultant solution with the hydrotalcite either by impregnation or slurry mixing and then drying the resultant mixture. Suitable rare earth metal compounds include acetates, halides, oxides, oxyhalides, hydroxides, sulfides, sulfonates, borides, borates, carbonates, nitrates, carboxylates and mixtures thereof.

Where the catalyst composition contains a matrix and/or binder, the molecular sieve is conveniently initially formulated into a catalyst precursor with the matrix and/or binder and hydrotalcite composition is then combined with the formulated precursor. In one embodiment, the molecular sieve composition and the matrix material, optionally with a binder, are combined with a liquid to form a slurry and then mixed, such as by colloid milling, to produce a substantially homogeneous mixture containing the molecular sieve composition. Non-limiting examples of suitable liquids include one or a combination of water, alcohol, ketones, aldehydes, and/or esters. The most preferred liquid is water.

The resultant catalyst composition can then be formed into useful shaped and sized particles by well-known techniques such as spray drying, pelletizing, extrusion, and the like.

Once the molecular sieve catalyst composition is formed in a substantially dry or dried state, to further harden and/or activate the formed catalyst composition, a heat treatment such as calcination, at an elevated temperature is usually performed. Typical calcination temperatures are in the range from about 400° C. to about 1,000° C., such as from about 500° C. to about 800° C., such as from about 550° C. to about 700° C. Typical calcination environments are air (which may include a small amount of water vapor), nitrogen, helium, flue gas (combustion product lean in oxygen), or any combination thereof.

Process for Using the Molecular Sieve Catalyst Compositions

The catalyst compositions described above are useful in a variety of processes including the conversion of a feedstock containing one of more aliphatic compounds, preferably oxygenates, to olefins and the conversion of a feedstock including one or more oxygenates and ammonia into alkyl amines, in particular methylamines.

The most preferred process of the invention is a process directed to the conversion of an aliphatic feedstock to one or more olefin(s). Typically, the feedstock contains one or more aliphatic-containing compounds such that the aliphatic moiety contains form 1 to about 50 carbon atoms, such as form 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, fornaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst composition of the invention is particularly useful in the process that is generally referred to as the gas-to-olefins (GTO) process or alternatively, the methanol-to-olefins (MTO) process. In this process, an oxygenated feedstock, most preferably a methanol-containing feedstock, is converted in the presence of a molecular sieve catalyst composition into one or more olefin(s), preferably and predominantly, ethylene and/or propylene.

Using the catalyst composition of the invention for the conversion of a feedstock, preferably a feedstock containing one or more oxygenates, the amount of olefin(s) produced based on the total weight of hydrocarbon produced is typically greater than 50 weight percent, for example greater than 60 weight percent, such as greater than 70 weight percent. Moreover, the amount of ethylene and/or propylene produced based on the total weight of hydrocarbon product produced is typically greater than 40 weight percent, such as greater than 50 weight percent, for example greater than 65 weight percent. Typically, the amount ethylene produced in weight percent based on the total weight of hydrocarbon product produced, is typically greater than 20 weight percent, such as greater than 30 weight percent. In addition, the amount of propylene produced in weight percent based on the total weight of hydrocarbon product produced is typically greater than 30 weight percent, such as greater than 40 weight percent.

In addition to the oxygenate component, such as methanol, the feedstock may contains one or more diluent (s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example from about 250° C. to about 800° C, including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 hr-1 to about 5000 hr-1, such as from about 2 hr-1 to about 3000 hr-1, for example from about 5 hr-1 to about 1500 hr-1, and conveniently from about 10 hr-1 to about 1000 hr-1. In one embodiment, the WHSV is greater than 20 hr-1 and, where feedstock contains methanol and/or dimethyl ether, is in the range of from about 20 hr-1 to about 300 hr-1.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. patent application Ser. No. 09/708,753 filed Nov. 8, 2000, which is herein incorporated by reference.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor types are riser reactors generally described in Riser Reactor, Fluidization and Fluid-Particle Systems, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system would conveniently include a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, O3, SO3, N2O, NO, NO2, N2O5, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are disclosed in U.S. Pat. No. 6,290,916 (controlling moisture), which is herein fully incorporated by reference.

The regenerated catalyst composition withdrawn from the regeneration system, preferably from a catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, Experimental Techniques, Circulating Fluidized Beds, Grace, Avidan and Knowlton, eds., Blackie, 1997 (336–337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a de-ethanizer, a depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominantly olefin(s), preferably light olefin(s) such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Using the catalyst composition of the invention for the conversion of a feedstock containing one or more oxygenates into olefin(s), it is found that the life of the catalyst is improved as compared with a similar catalyst without the hydrotalcite additive. Typically, the improvement is such that the life of the catalyst of the invention is at least 50%, such as at least 100%, for example at least 200%, greater than that of the catalyst without the hydrotalcite additive.

The catalyst composition described herein can also be used in the manufacture of alkylamines, using a feedstock including ammonia in addition to oxygenates. Examples of suitable processes are described in EP 0 993 867 A1, and in U.S. Pat. No. 6,153,798.

The invention will now be more particularly described with reference to the Examples, in which all parts are by weight.

EXAMPLE 1

Synthesis of EMM-2

To 165.5 parts of demineralized water were added 228.4 parts of an 85% solution of H3PO4. 103 parts of water were used to rinse the container. To this diluted solution were added 14.9 parts of Ludox AS40 and 2.1 parts of water were used to rinse the container. Then 416.7 parts of a 35% solution of TEAOH (tetraethylammonium hydroxide) were added and 24.8 parts of rinse water were used to rinse the container. Finally 133.2 parts of Condea Pural SB were added and mixed until a homogeneous mixture was obtained, whereafter the container was rinsed with 4.1 parts of water.

The resultant homogeneous mixture was crystallized in a stirred autoclave with stirring rate of 50 rpm. The autoclave was heated in 12.5 hours to 175° C. and was kept at that temperature for 50 hours to effect the crystallization. The resultant EMM-2 crystals were recovered by washing and drying. After drying the material overnight at 120° C., 21.3 wt % (based on the initial intake) of solids were recovered. The resultant material was then calcined first in nitrogen at 650° C. for 5 hours, followed by air calcination for 3 hours at 650° C.

EXAMPLE 2

EMM-2 with La/Hydrotalcite 0.23 gram of lanthanum acetate was dissolved in 1.9 ml of de-ionized water and the resulting solution was added drop-wise to 2.015 gram of hydrotalcite as supplied by Sasol North America Inc. as Condea Pural MG70 (specific surface area of 180 m2/gram). The treated hydrotalcite was dried at 50° C. for 1 hour under vacuum and then calcined in air at 550° C. for 3 hours.

0.2 gram of the La-impregnated hydrotalcite was mixed with 0.36 gram of the calcined EMM-2 from Example 1 and the resultant catalyst was evaluated in the conversion of methanol to olefins in a fixed bed reactor equipped with an on-line gas chromatograph for product analysis. The test conditions were 450° C., 25 psig (273 kPaa) and 25 WHSV. The results of the test are summarized in Table 1 which also shows the results obtained with a comparative test using 0.36 gram of EMM-2 alone under the same conditions.

TABLE 1

| Catalyst | EMM-2 | EMM-2 + La/Hydrotalcite |
|---|---|---|
| $C_2$ = (wt % of product) | 35.3 | 32.3 |
| $C_3$ = (wt % of product) | 41.0 | 43.7 |
| $C_2$ = +$C_3$ = (wt % of product) | 76.3 | 76.0 |
| Catalyst Life | 20.7 | 72.3 |

It is clear from Table 1 that the addition of the La/hydrotalcite to the EMM-2 increased the life of the catalyst and also increased its propylene selectivity at the expense of its ethylene selectivity. The total ethylene plus propylene selectivity was substantially unaffected. The catalyst life is defined as the total amount of methanol converted in grams per gram of EMM-2.

EXAMPLE 3

Synthesis of Ge APO-34/18 Intergrowth 21.8 grams of H3PO4 (85%) were diluted with 22.1 grams of de-ionized water and to this solution were added 3.6 grams of Ge-ethoxide. After mixing this solution, 40.1 grams of TEAOH (35%) were added dropwise to the solution, whereafter 12.8 grams of Condea Pural SB were added and mixed until a homogeneous mixture was obtained. 85.8 grams of this mixture was transferred to a 150 ml stainless steel autoclave and mounted on an axis inside a oven. The autoclave was rotated at 60 rpm while the oven was heated in 8 hours from room temperature to 175° C. and then kept at this temperature for 48 hours. After crystallization, the resultant GeAPO-34/18 intergrowth product was washed and dried. 18.9 wt % of solid yield was recovered after drying overnight at 120° C. The AEI/CHA of ratio of the recovered intergrowth material was 90:10. The final product was calcined first in nitrogen at 650° C. for 5 hours, followed by air calcination for 3 hours at 650° C.

EXAMPLE 4

Ge-APO34/18 with La/Hydrotalcite 0.61 gram of lanthanum chloride was dissolved in 4.72 ml of de-ionized water and the resulting solution was added drop-wise to 5.00 gram of hydrotalcite as supplied by Sasol North America Inc. as Condea Pural MG70 (specific surface area of 180 m2/gram). The treated hydrotalcite was dried at 50° C. for 1 hour under vacuum and then calcined in air at 550° C. for 3 hours.

0.2 gram of the La-impregnated hydrotalcite produced above was mixed with 0.36 gram of the calcined GeAPO-34/18 of Example 3 and the resultant catalyst was evaluated in the conversion of methanol to olefins in a fixed bed reactor equipped with an on-line gas chromatograph for product analysis. The test conditions were 450° C., 25 psig (273 kPaa) and 25 WHSV. The results of the test are summarized in Table 2 which also shows the results obtained under the same conditions with (a) a catalyst consisting solely of 0.36 gram of GeAPO-34/18 and (b) a catalyst comprising 0.36 gram of GeAPO-34/18 and 0.2 gram of calcined hydrotalcite (no La impregnation).

TABLE 2

| Catalyst | GeAPO-34/18 | GeAPO-34/18 + Hydrotalcite | GeAPO-34/18 + La/Hydrotalcite |
|---|---|---|---|
| $C_2=$ (wt % of product) | 31.5 | 29.4 | 27.9 |
| $C_3=$ (wt % of product) | 43.6 | 44.3 | 46.3 |
| $C_2= +C_3=$ (wt % of product) | 75.0 | 73.7 | 74.2 |
| Catalyst Life | 38.9 | 82.0 | 107.9 |

It is clear from Table 2 that the addition of the hydrotalcite to the GeAPO-34/18 increased the life of the catalyst by over 100%, whereas the addition of La/hydrotalcite increased the life of the catalyst by over 170%.

While the present invention has been described and illustrated by reference to particular embodiments, those of ordinary skill in the art will appreciate that the invention lends itself to variations not necessarily illustrated herein. For example, it is contemplated that the catalyst compositions described herein are useful in other processes, such as catalytic cracking. For this reason, reference should be made solely to the appended claims for purposes of determining the true scope of the present invention.

What is claimed is:

1. A catalyst composition comprising a molecular sieve selected from silicoaluminophosphates, aluminophosphates, metal-containing forms thereof and mixtures, including intergrowths, thereof, hydrotalcite, and a rare earth metal component.

2. The catalyst composition of claim 1, wherein the molecular sieve is selected from silicoaluminophosphates, metal-containing forms thereof and mixtures, including intergrowths, thereof.

3. The catalyst composition of claim 1, wherein the molecular sieve is selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, MCM-2, metal-containing forms thereof, and mixtures, including intergrowths, thereof.

4. The catalyst composition of claim 1, wherein the molecular sieve is selected from SAPO-18, SAPO-34, SAPO-35, SAPO-44, SAPO-47, ALPO-34, metal-containing forms thereof, and mixtures, including intergrowths, thereof.

5. The catalyst composition of claim 1, wherein the molecular sieve is SAPO-34, SAPO-18, an intergrowth of SAPO-34 and SAPO-18, GeAPO-34, GeAPO-18 or an intergrowth of GeAPO-34 and GeAPO-18.

6. The catalyst composition of claim 1, wherein the rare earth metal is lanthanum.

7. The catalyst composition of claim 1, wherein the composition comprises from 10 to 90 wt % of the molecular sieve, from 10 to 90 wt % of the hydrotalcite, and from 0.1 to 5 wt % of the rare earth metal component, wherein the weight percents are based on the total weight of the molecular sieve, the hydrotalcite, and the rare earth metal component.

8. A catalyst composition comprising:
   (a) an aluminophosphate or silicoaluminophosphate molecular sieve selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, MCM-2, metal-containing forms thereof, and mixtures, including intergrowths, thereof; and
   (b) hydrotalcite.

9. The catalyst composition of claim 8, wherein the molecular sieve is selected from SAPO-18, SAPO-34, SAPO-35, SAPO-44, SAPO-47, ALPO-34, metal-containing forms thereof, and mixtures, including intergrowths, thereof.

10. The catalyst composition of claim 8, wherein the molecular sieve is SAPO-34, SAPO-18, an intergrowth of SAPO-34 and SAPO-18, GeAPO-34, GeAPO-18, or an intergrowth of GeAPO-34 and GeAPO-18.

11. The catalyst composition of claim 8, comprising the molecular sieve in an amount of from 10 to 90 wt %, and the hydrotalcite in an amount of from 10 to 90 wt %, wherein the weight percents are based on the total weight of the molecular sieve and the hydrotalcite.

12. The catalyst composition of claim 8, further comprising a rare earth metal component.

13. The catalyst composition of claim 12, comprising the molecular sieve in an amount of from 10 to 90 wt %, the hydrotalcite in an amount of from 10 to 90 wt %, and the rare earth metal component in an amount of from 0.1 to 5 wt %, wherein the weight percents are based on the total weight of the molecular sieve, the hydrotalcite and the rare earth metal component.

14. The catalyst composition of claim 12, wherein the rare earth metal component is lanthanum.

15. A process for producing a molecular sieve catalyst composition, the process comprising:
   (a) providing a molecular sieve selected from silicoaluminophosphates, aluminophosphates, metal-containing forms thereof and mixtures, including intergrowths, thereof;
   (b) providing a hydrotalcite composition comprising hydrotalcite and a rare earth metal component; and
   (c) combining the molecular sieve and the hydrotalcite composition to produce a molecular sieve catalyst composition.

16. The process of claim 15, wherein the molecular sieve is selected from silicoaluminophosphates, metal-containing forms thereof and mixtures, including intergrowths, thereof.

17. The process of claim 15, wherein the molecular sieve is selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAP-47, SAPO-56, AlPO-5, AlPO-11, AlPO-18, AlPO-31, AlPO-34, AlPO-36, AlPO-37, AlPO-46, MCM-2, metal-containing forms thereof, and mixtures, including intergrowths, thereof.

18. The process of claim 15, wherein the molecular sieve is selected from SAPO-18, SAPO-34, SAPO-35, SAPO-44, SAPO-47, ALPO-34, metal-containing forms thereof, and mixtures, including intergrowths, thereof.

19. The process of claim 15, wherein the molecular sieve is SAPO-34, an intergrowth of SAPO-34 and SAPO-18, or GeAPO-34.

20. The process of claim 15, wherein the rare earth metal component is lanthanum.

21. The process of claim 15, wherein the molecular sieve catalyst composition comprises from 10 to 90 wt % of the molecular sieve, from 10 to 90 wt % of the hydrotalcite, and from 0.1 to 5 wt % of the rare earth metal component, wherein the weight percents are based on the total weight of the molecular sieve, the hydrotalcite, and the rare earth metal component.

22. The process of claim 15, wherein the step of providing a hydrotalcite composition comprises:
(i) providing a solution of a rare earth metal compound;
(ii) treating hydrotalcite with said solution; and
(iii) drying the treated hydrotalcite to form a dried hydrotalcite composition.

23. The process of claim 22, wherein the rare earth metal compound is selected from halides, oxides, oxyhalides, hydroxides, sulfides, sulfonates, borides, borates, carbonates, nitrates, carboxylates and mixtures thereof.

24. The process of claim 22, wherein the solution is an aqueous solution.

25. The process of claim 22, further comprising (iv) calcining the dried hydrotalcite composition.

26. The process of claim 15, wherein the step of combining comprises:
(i) forming a slurry comprising the molecular sieve and the hydrotalcite composition; and
(ii) drying the slurry to form a dried, formulated molecular sieve catalyst composition.

27. The process of claim 26, wherein the slurry comprises a liquid, molecular sieve, hydrotalcite and a rare earth metal compound.

28. The process of claim 27, wherein the rare earth metal compound is selected from halides, oxides, oxyhalides, hydroxides, sulfides, sulfonates, borides, borates, carbonates, nitrates, carboxylates and mixtures thereof.

29. The process of claim 27, wherein the rare earth metal compound is soluble in the liquid.

30. The process of claim 27, wherein the rare earth compound and the hydrotalcite are pre-contacted to form the hydrotalcite composition.

31. The process of claim 30, wherein the step of pre-contacting comprises:
(i) providing a solution of a rare earth metal compound;
(ii) treating hydrotalcite with said solution; and
(iii) drying the treated hydrotalcite to form a dried hydrotalcite composition.

32. The process of claim 27, wherein the liquid comprises at least one of water, an alcohol, a ketone, an aldehyde, or an ester.

33. The process of claim 26, wherein the step of drying comprises spray drying.

* * * * *